(12) United States Patent
Jones

(10) Patent No.: US 10,980,482 B2
(45) Date of Patent: Apr. 20, 2021

(54) SAMPLING CAPSULE SYSTEM AND METHODS

(71) Applicant: James Phillip Jones, Sudan, TX (US)

(72) Inventor: James Phillip Jones, Sudan, TX (US)

( * ) Notice: Subject to any disclaimer, the term of this patent is extended or adjusted under 35 U.S.C. 154(b) by 0 days.

(21) Appl. No.: 16/711,342

(22) Filed: Dec. 11, 2019

(65) Prior Publication Data

US 2020/0113521 A1 Apr. 16, 2020

Related U.S. Application Data

(63) Continuation-in-part of application No. 16/477,882, filed as application No. PCT/US2018/064141 on Dec. 5, 2018.

(60) Provisional application No. 62/682,091, filed on Jun. 7, 2018, provisional application No. 62/573,578, filed on Dec. 6, 2017.

(51) Int. Cl.
*A61B 5/00* (2006.01)
*A61B 10/00* (2006.01)

(52) U.S. Cl.
CPC .......... *A61B 5/6861* (2013.01); *A61B 5/0031* (2013.01); *A61B 10/0038* (2013.01); *A61B 10/0045* (2013.01); *A61B 2010/0061* (2013.01); *A61B 2562/0285* (2013.01); *A61B 2562/08* (2013.01)

(58) Field of Classification Search
CPC . A61B 5/0031; A61B 5/6861; A61B 10/0045; A61B 10/0038; A61B 2010/0061; A61B 2562/08; A61M 31/002
See application file for complete search history.

(56) References Cited

U.S. PATENT DOCUMENTS

| | | | |
|---|---|---|---|
| 4,481,952 A | * | 11/1984 | Pawelec ............... A61B 10/00 600/582 |
| 5,316,015 A | | 5/1994 | Sinaiko |
| 8,394,034 B2 | | 3/2013 | Iddan |
| 8,491,495 B1 | | 7/2013 | Shuck |
| 9,072,583 B2 | | 7/2015 | Brister et al. |
| 9,375,202 B2 | | 6/2016 | Swain et al. |
| 9,687,638 B2 | | 6/2017 | Progenity |
| 9,907,755 B2 | | 3/2018 | Kabadi |
| 9,980,905 B2 | | 5/2018 | Buydts et al. |

(Continued)

OTHER PUBLICATIONS

Ingestable Osmotic Pill form In Vivo Sampling of Gut Microbiomes, Advanced Intelligent Systems, 1, 1900053, Aug. 2019, Hotatollah Nejad et al.

*Primary Examiner* — Max F Hindenburg
(74) *Attorney, Agent, or Firm* — Arno Naeckel

(57) ABSTRACT

A non-invasive system for sampling gastrointestinal microbiota with their associated environment for discovery, characterization, medical research, diagnostics, and treatment using an ingestible, non-digestible sampling capsule. The capsule device, with ports open for acquiring a sample of gastrointestinal microbiota and content, is placed inside an immediate or delayed release capsule. When the outer capsule dissolves according to its specifications, enteric fluid and content enters the sampling capsule through the ports triggering a hydrophilic stop to release a pulling force to close the ports by enveloping the capsule outer casing over the inner casing, capturing the sample, and holding it sealed until it completes passage through the digestive track, and is recovered from feces for analysis.

21 Claims, 11 Drawing Sheets

(56) References Cited

U.S. PATENT DOCUMENTS

| | | | |
|---|---|---|---|
| 10,098,571 B2 | 10/2018 | Liu | |
| 10,172,598 B2 * | 1/2019 | Amoako-Tuffour | ......................... A61B 10/04 |
| 10,369,111 B2 | 8/2019 | Kabadi | |
| 10,632,251 B2 | 4/2020 | Imran et al. | |
| 10,674,899 B2 | 6/2020 | Trollsas et al. | |
| 10,722,220 B2 * | 7/2020 | Jones | ................. A61B 10/0045 |
| 2004/0097834 A1 | 5/2004 | Stoltz | |
| 2011/0046458 A1 * | 2/2011 | Pinedo | ..................... A61B 5/07 600/309 |
| 2015/0182169 A1 * | 7/2015 | Kostenich | ............ A61B 5/4255 600/476 |
| 2016/0038086 A1 * | 2/2016 | Wrigglesworth | .. A61B 5/14539 600/361 |
| 2017/0118856 A1 * | 4/2017 | Blunier | .............. B23K 26/0624 |
| 2017/0252018 A1 * | 9/2017 | Wrigglesworth | .. A61B 10/0045 |
| 2019/0223846 A1 * | 7/2019 | Kerkhof | ................. A61B 10/04 |
| 2019/0274663 A1 * | 9/2019 | Rees | ................. A61B 10/0045 |
| 2019/0298318 A1 | 10/2019 | Cinquin et al. | |
| 2019/0343425 A1 | 11/2019 | Jones et al. | |
| 2019/0374207 A1 * | 12/2019 | Jones | ...................... A61B 5/42 |
| 2020/0038000 A1 * | 2/2020 | Wang | ................. A61M 31/002 |
| 2020/0146541 A1 * | 5/2020 | Yangdai | ................ A61B 1/041 |

* cited by examiner

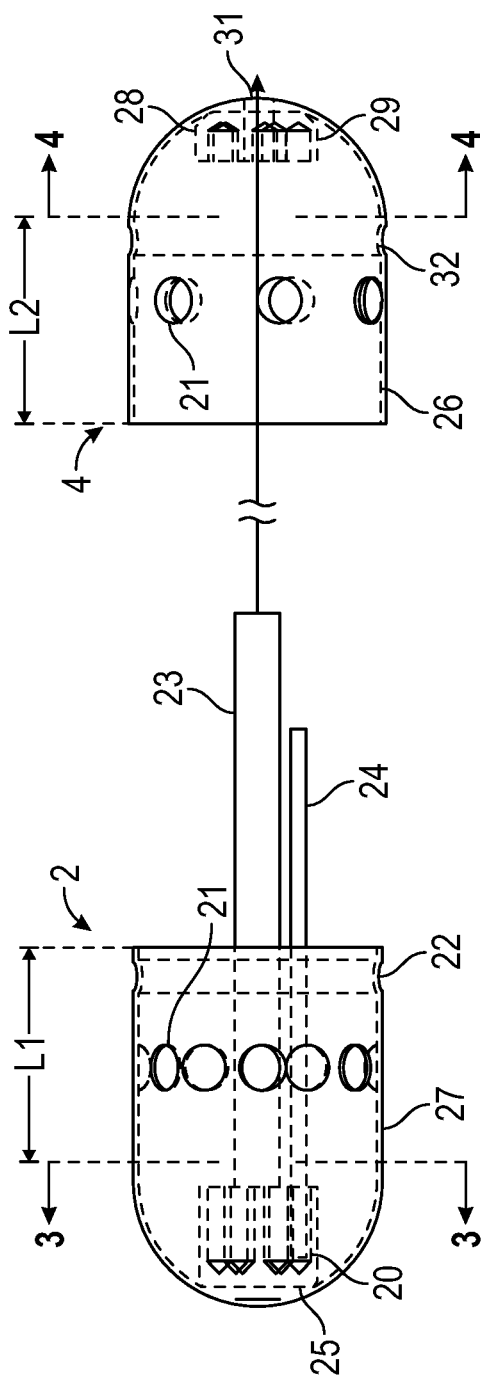
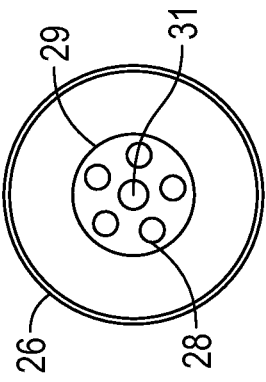
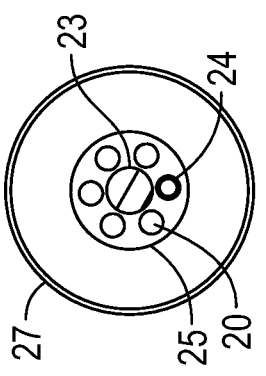

SAMPLING CAPSULE SYSTEM AND METHODS

PRIORITY APPLICATIONS

The present Continuation-in-Part application claims priority from U.S. Utility application Ser. No. 16/477,882 filed on Jul. 13, 2019 that in turn claims priority from Paris Cooperation Treaty (PCT) application PCT/US2018/64141 filed on Dec. 5, 2018 that in turn claims priority from both U.S. provisional applications 62/573,578 filed on Dec. 6, 2017 and 62/682,091 filed on Jun. 7, 2018, all of which are incorporated herein by reference in their entireties.

BACKGROUND OF THE INVENTION

Field of Invention

The present invention relates to at least one device, at least one system, and at least one process or method to be used within the medical sciences, engineering, research and medical technologies. The device is ingestible, untethered, and is designed to collect samples from, or release substances into, a gastrointestinal tract.

Description of the Related Art

Major scientific research and medical efforts are being dedicated to discovering an ever increasing amount of knowledge regarding the roles played in human and animal life and disease by gastrointestinal microbes. An individual's gastrointestinal microbiome varies with location and time due to a multitude of factors including symbiosis and antibiosis relationships, time, ingesta, age, and health. Microbiota taxa vary from location to location in the digestive tract becoming increasingly diverse and abundant through the differing stages of the digestive tract from the stomach to the colon. One published estimate indicates that approximately $10\infty$ microbes are found in the small intestine and $10^{\wedge}10$ microbes (or 50% of the fecal mass) are found in the colon. The nature of the microbes and their function remain much of a mystery due to inaccessibility of the gut, the lack of an effective means to sample and characterize them, and the complex symbiotic relationships in their localized taxa.

Medicine has advanced in all major human body systems, such as cardiovascular, neurological, muscular and skeletal, but the intestinal tract still remains much of a mystery. Though there are instruments and devices which can be used for endoscopy/colonoscopy, there are sections of intestines that remain unexplored and are found incredibly difficult to collect and preserve samples there from. Even these upper and lower extremities, which can be viewed by camera and can only be treated for visible damage, such as polyps or ulcers. One known device is a camera pill that can now be swallowed and pictures taken throughout the intestinal tract, but visible inspection does not address the scientific mysteries of diseases and their causes or cures.

The human gut represents a void in medical science. The roles that bacteria play in the intestinal tract are poorly understood, except that there are "good" and "bad" bacteria. In fact, only a few of the estimated thousands of strains of bacteria are known, or have been identified, have been characterized and their roles determined. An aim of the subject matter disclosed herein is to help answer questions such as: what biochemical products exist for any specific diet as a function of the gut length x; what biochemical reactions take place along the gut length x; what microbes exist at any point within the gut anatomical system; what are the byproducts of all microbes including their toxins, exotoxins and endotoxins, and virulence factors and enzymes existing within the gut.

Further, the interaction of a) the normal biochemical reactions, b) the microbes, and c) the microbe byproducts are largely unknown, and believed to be a major source of several major diseases. Some 15 categories of bacteria have been broadly identified within the Phylogenic Tree as existing within major components of the gastrointestinal tract. Thus, in general, bacteria strains and colonies and their populations, population densities, habitats, and characteristics and contributions to the digestive process are only vaguely known in healthy individuals, and largely unknown in unhealthy individuals, much less as a function of gut length x.

The inaccessible regions of the most important anatomy of the gut, the lack of technology to explore, discover, and experiment in an in vivo manner, and then administer medications and measure in vivo the immediate results, has constrained the advance of medical science pertaining to the gut. A competent research effort investigating any animate or inanimate system should attempt to identify the fundamental multidisciplinary scientific principles of science and engineering upon which the system is based and functions, and then develop quantitative measures of those principles. The inaccessibility of the gut, and the heretofore lack of exploratory technology, has resulted in speculation and statistical correlation of symptoms from a distance throughout history as a means of researching the gut. The need for in vivo technology became immediately apparent. The first step to further this technology is the determination of what exists at various distances x along the gastrointestinal tract.

Non-invasive sampling processes are presently limited to oral spit, internal swabs, and feces analysis. Minimal invasive sampling processes include swabs of the rectum. They do not provide for examination of localized microbiota community content within the gut that is important to gain understanding of bacteria and host-bacterial interactions. This problem is complicated by changing environmental conditions such as pH, the release of resident bacteria and other microbiota (alive and dead), body chemistry, particles, and fluids from upstream regions of the gastrointestinal tract that transit through the intestines and are subsequently detectable in feces. The intraluminal pH rapidly changes from highly acidic in the stomach (pH 1-3.5) to about pH 6 in the duodenum. The pH gradually increases in the small intestine from pH 6 to about pH 7.4 in the terminal ileum. The pH drops to 5.7 in the caecum, but again gradually increases, reaching pH 6.7 in the rectum. Feces confounds characterization of microbial communities that are extremely diverse and include a large number of Gram-positive eubacteria, Gram-negative bacteria, cyanobacteria, archaea, fungi, protozoa, and virus as luminal communities within the colon that differ, for example, from dynamic mucosa-associated communities found in the small intestine.

Invasive gastroscopy and endoscopy procedures are used to sample microbiota of the upper gastrointestinal track of the esophagus, stomach, and duodenum and for the lower intestinal tract of the colon, large intestine, and lower portion of small intestine, but approximately 5 m of ileum and jejunum cannot be reached for scope sampling. Both scopes necessitate expensive procedures and require anesthesia, risk, and recovery in a medical setting. They are a poor strategy for time course data acquisition, diagnosis support, or treatment support.

Efforts to find an effective method to sample intestinal microbiota in their local areas have not been successful. Indeed citations show there have been inventive efforts including ingestible capsules operated with electrical circuits, batteries, radio, magnetic fields, steel compression and torsion springs working alone or together, and vacuums. Examples of such contributions may be found in U.S. Pat. Nos. 8,491,495, 8,915,863, 8,926,526, 9,215,997, and 9,955,922 to Shuck and all of which are included herein by reference in their entireties. However, these devices and methods are not in present use and appear to be impractical for production or general use. Research, medical communities, and patients beg novel solutions that can be repetitively used at home or in a general medical practice setting.

The subject matter herein comprises mechanical devices, systems, and methods for acquiring samples of matter along an intestinal track of a user in-vivo. The device is a capsulized device and system configured to be swallowed and passed through the intestinal track. The device comprises a hollow casing or housing defining one or more openings adapted to allow samples of liquid and semi-liquid matter to pass into the housing during a specified time interval and then sealed therein for collection outside the body for analysis. Further, some embodiments are capable of releasing substances stored within the device into the surrounding environment.

SUMMARY

The subject matter presented herein describes a sampling system comprising an inner capsule and an outer casing. The inner casing comprises a ported first casing with an open end, a closed end, an inner surface, and an outer surface and a ported second casing with an open end, a closed end, an inner surface, and an outer surface. The system further comprises a hydrophobic, acid resistant elastomeric filament fixedly attached to the closed end of the ported first casing and to the closed end of the ported second casing, a hydrophilic strut, wherein the hydrophilic strut spaces the closed end of the ported first casing away from the closed end of the ported second casing and is of such a length as to impart a tension in the hydrophobic elastomeric filament; and a first digestible outer capsule enveloping the inner capsule, the first digestible outer capsule being configured to temporarily isolate the inner capsule from bodily fluids.

The subject matter presented herein also describes a gastrointestinal sampling device comprising a hollow capsule having a ported inner casing with a closed end and an open end and having a ported outer casing with a closed end and an open end, an elastomeric filament fixedly securing the closed end of the inner casing to the closed end of the outer casing; and a hydrophilic strut spacing the closed end of the inner casing away from the closed end of the outer casing when intact.

The subject matter presented here in further describes a gastrointestinal sampling system comprising a hollow capsule having a ported inner casing having a closed end and an open end slidingly engaged within a ported outer casing also having a closed end and an open end; and, an elastomeric filament fixedly securing the closed end of the inner casing to the closed end of the outer casing.

BRIEF DESCRIPTIONS OF THE DRAWINGS

FIG. 1 depicts a perspective view of an exemplary ported inner casing of the gastrointestinal sampling device according to an embodiment.

FIG. 2 depicts a perspective view of an exemplary ported outer casing of the gastrointestinal sampling device according to an embodiment.

FIG. 3 depicts a cross-sectional view of an exemplary ported inner casing of the gastrointestinal sampling device according to an embodiment.

FIG. 4 depicts a cross-sectional view of an exemplary ported outer casing of the gastrointestinal sampling device according to an embodiment.

DETAILED DESCRIPTION

Figure 5:
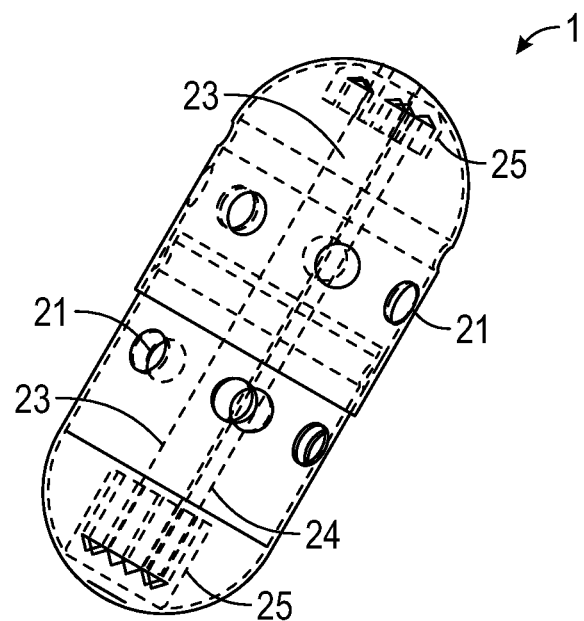
FIG. 5 depicts a perspective view of an assembled gastrointestinal sampling device in the strutted, open configuration.

The following detailed description is merely exemplary in nature and is not intended to limit the invention, or the application, or uses of the subject matter disclosed. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

It should be understood that the terms "right" and "left" are used solely to denote opposite sides of an element, component, or surface in the same manner that "top" and "bottom" are used solely to denote opposite sides of an element, component, or surface and should not unnecessarily be construed as limiting the position or orientation of said element, component, or surface.

In the following description, for purposes of explanation, numerous specific details are set forth in order to provide a thorough understanding of the present invention. It will be evident, however, to one skilled in the art that the present invention may be practiced without these specific details.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

Reference should now be made to the drawings in which the same reference numbers are used throughout the various figures to designate the same or similar components. FIG. 1 (inner casing 2) and FIG. 2 (outer casing 4) are each one-piece acid tolerant medicinal grade elastomer or metallic devices with ports or holes 21 that penetrate through casing walls 27 and 26, respectively. When assembled, the inner casing 2 and the outer casing 4 comprise the gastrointestinal sampling device 1 (See, FIG. 5). The inner casing 2 and the outer casing 4 may be circular cylinders, each with a domed closed end portion to ease transit though the digestion system. Each casing may also be referred to as a "half-capsule"). However, different shapes may be employed that provide efficient or structural advantage in a given situation, including a simple sphere.

As a non-limiting example, a gastrointestinal sampling device 1 may have an open configuration length of approximately 24 mm and a closed configuration length of approximately 20 mm. The inner casing 2 may have a diameter of approximately 9.0 mm. The outer casing 4 may have a diameter of approximately 9.91 mm. When in the closed configuration, the volume of the enclosed sample may be approximately 0.50 ml or eight (8) drops of fluid sample. The material of the gastrointestinal sampling device 1 may be a molded biomedical ingestible grade elastomer with a Shore A hardness of approximately 40.

The number of ports 21, their size, shape, or their configuration on the casings may be varied to satisfy sample collection or material delivery efficacy. However, it should be noted that the casing walls 26 and 27 are of such lengths L1 and L2 so as to cover and effectively seal the ports 21 in the other casing's walls such that all of the ports 21 in the gastrointestinal sampling capsule are fluid tight to ensure that the sample enclosed therein does not leak out after the time of closing. In some equivalent embodiments either the inner casing 2 or the outer casing 4 may have no ports 21 (See, e.g., FIG. 20).

Each of the inner casing 2 and outer casing 4 may include its own receiver 25 and 29, respectively. Receivers 25 and 29 may be used to guide and support a strut 24 within one pair of multiple channels 20 and 28, respectively.

In some embodiments, strut 24 may be physically fashioned out of a single piece of medical grade hydrophilic material such that the hydrophilic action strut 24 rapidly fails upon contact with a specified bowel material, acid, chemical or with fluids generally. Alternatively, the strut 24 may be engineered to fail after a period of time (a delayed action strut) rather than immediately (an immediate action strut). The time to fail may be controlled by the choice of material, the physical shape of the strut or both. One such material may be cellulose. Other possible non-limiting materials include polyvinyl alcohol, seaweed derivatives from the Evoware Company of Indonesia, casein proteins developed by the US Department of Agriculture, Agar, and the root of the cassava plant produced by the Avani Company of Bali. In short, any suitable medical grade dissolvable/digestible material may be used that currently exists or that may be developed in the future. The term "digestible" as used herein in regard to an outer capsule means "able to be softened or decomposed by heat and moisture or chemicals," such as may be found in the digestive tract. The term "ingestible" means "swallowable."

Figure 12:
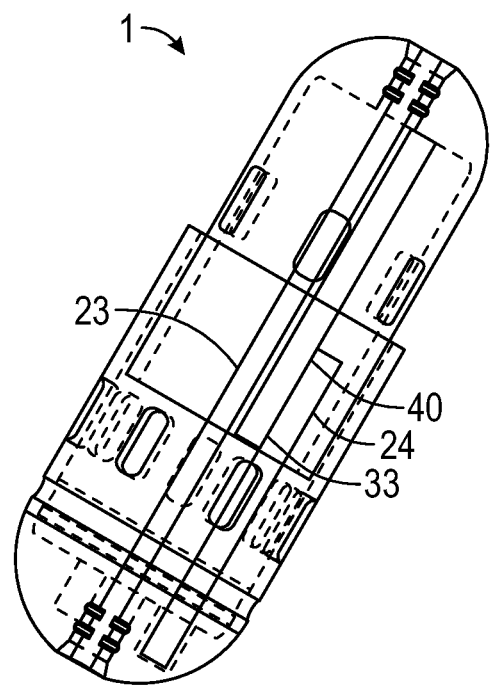
FIG. 12 is a perspective view of the assembled gastrointestinal sampling device of FIG. 10 in its open configuration.
Figure 13:
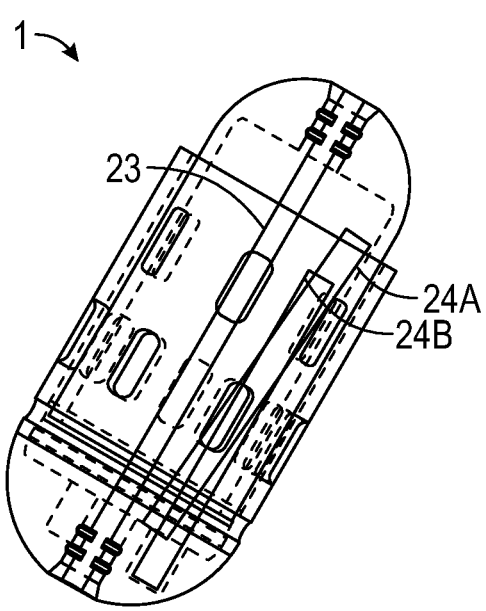
FIG. 13 is a perspective view of the assembled gastrointestinal sampling device of FIG. 10 in its closed configuration.

In other embodiments (See, e.g. FIGS. 12-13), strut 24 may be comprised of two or more hydrophobic members (24A-B) temporally connected by an attachment means 40 such as an adhesive, a pin, or similar means that may currently exist or be developed in the future. In some embodiments the attachment means may be a hydrophilic attachment means such that bowel material or fluid attacks only the attachment means 40 and not the hydrophobic members themselves that are allowed to subsequently detach. This multiple piece embodiment of strut 24 may also be referred to a hydrophilic action strut 24 but may be claimed in alternative language such as an immediate release strut. In other embodiments the attachment means 40 may be comprised of a pH sensitive material and may be termed a pH attachment means or a delayed action connection means. A non-limiting example of an adhesive suitable for purpose of attaching two hydrophobic struts is polyvinyl alcohol (PVOH), which may be both a hydrophilic attachment means and a pH attachment means.

As a non-limiting example the strut 24 has a length L that may be of approximately 20.5 mm and a diameter of 1.3 mm. Strut 24 may be a cylinder or a parallelepiped and may be further shaped to tailor the timing of its failure to a desired time period, including immediate failure upon contact with an intestinal fluid.

In some embodiments, inner casing 2 and outer casing 4 are mated by inserting one end of strut 24 into one of the channels (20, 28) in receiver (25, 29) of one casing (2, 4) and the other end into a corresponding channel (20, 28). The number of channels (20, 28) may vary but there must be at least one channel in one of the two casings. In some embodiments, the closed ends of the inner casing 2 and the outer casing 4 may each include a hole 31 penetrating through both of the center of the receiver and the center of closed end of each casing to accept and pass through an elastomeric filament 23.

Elastomeric filament 23 may be attached to the same receivers (25, 29) as the strut 24 in both the inner and outer casings and is partially relaxed until both ends of strut 24 engage one of the channels (20, 28) in a casing, thereby requiring elastomeric filament 23 to stretch. In some embodiments the elastomeric filament 23 extends through the receiver(s) (25, 29) and into a hole 31 in the closed end(s) of one or both casings (2, 4) and is attached therein. The end of elastomeric filament 23 may be tensioned and then affixed to the walls of the receiver defining the hole 31 by welding or gluing to make the hole(s) 31 fluid tight. A non-limiting example of a glue for this purpose is Cyanoacrylate. A non-limiting example of elastomeric filament 23 may be comprised of Elastostar R 401/40 from Elastostar Rubber Company of Columbus Ohio, which may be tensioned to 80% of its elastic limit in this application.

In other equivalent embodiments, channels (20, 28) may be dispensed with and the strut 24 may be configured of such a length that merely loosely placing the strut 24 in the capsule serves to engage the closed ends of the inner and outer casings, space the inner casing and the outer casing apart, and tension the elastomeric filament 23.

Figure 6:
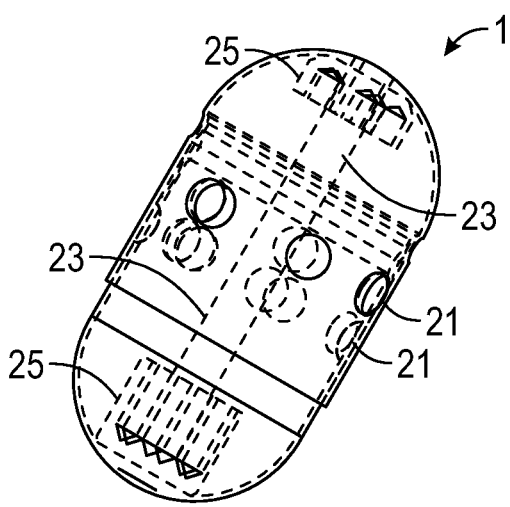
FIG. 6 depicts a perspective view of the gastrointestinal sampling device in the closed configuration.

When the inner casing 2 is partially inserted into the outer casing 4 and spaced apart by the strut 24 with a length L, the elastomeric filament 23 may be trimmed flush to the outer surface of casing (2, 4). The length L of strut 24 is such that when inserted it maintains the gastrointestinal sampling device 1 in its open configuration with all ports 21 unobstructed while imparting a tension in the elastomeric filament 23 (see, FIG. 5). The tension strains against the strut to place the gastrointestinal sampling device 1 into its closed configuration (see, FIG. 6) when the strut collapses. It should be noted that the elastomeric filament 23 is of a relaxed length that is less than the distance between receivers (25, 29) in a closed configuration such that it continues to maintain the inner casing 2 and outer casing 4 into the closed configuration in the absence of an intact strut 24.

In some embodiments the elastomeric filament 23 is comprised of an elastomer that is non-reactive to, or it is at least resistant to digestion by, bodily fluids. In some cases the elastomeric filament 23 may be notably acid resistant if it is to operate in the stomach where the gastric environment is at a pH of 3.0 and lower. A non-limiting example of a substance that is suitable for the elastomeric filament 23 is a medical grade silicone rubber, a non-limiting example of which is Elastostar R 401/40.

Strut 24 holds the assembled gastrointestinal sampling device 1 in its open configuration, or open port position, against the pulling tension provided by the elastomeric filament 23 until the strut 24 is weakened by inflowing enteric fluids and collapses thereby allowing the pulling tension to further encourage travel of outer casing 4 over inner casing 2 to close ports 21 by overlap of the casings. The two casings are secured in the closed configuration by a male locking stop ring 32 in one of the casings that is configured to lock by interference fit into the female locking stop ring 22 in the other casing. The residual tension remaining in elastomeric filament 23 insures that the gastrointestinal sampling device 1, and the capsule ports 21, remain closed while the gastrointestinal sampling device 1 and it captured sample is recovered. Instead or, or in addition to, an O-ring may also be employed to help seal the device in its closed configuration.

Figure 17:
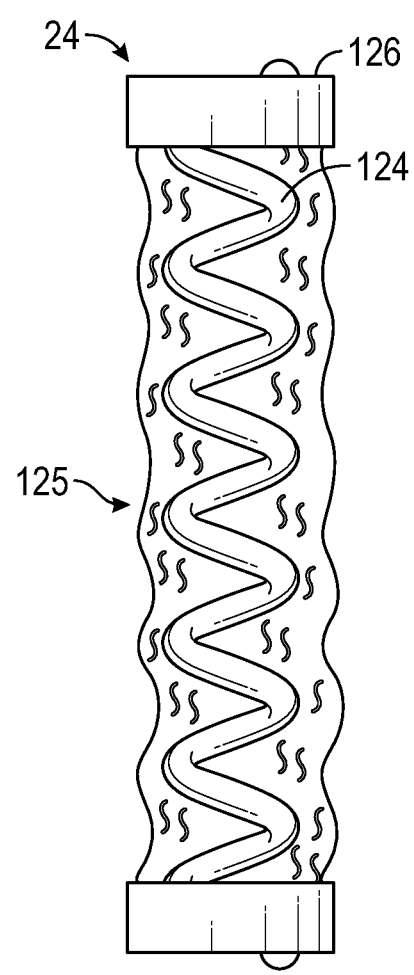
FIG. 17 is a depiction of a strut comprising an extended spring held in an elongated position by a hydrophilic substance.

In other equivalent embodiments (See FIG. 17) the strut 24 may be replaced with a spring 124 in an extended stressed condition. The extended condition of the spring 124 may be maintained by encasing the stressed spring in a medical grade hydrophilic immediate or delayed release material such as PVOH 125. When the PVOH is eroded away by the contact of bodily fluids, the spring is then able to contract to close the capsule 1. Both ends of extended spring include mounting plates 126 that attach the extended spring 124 to each of the inner casing and the outer casing.

Figure 18:
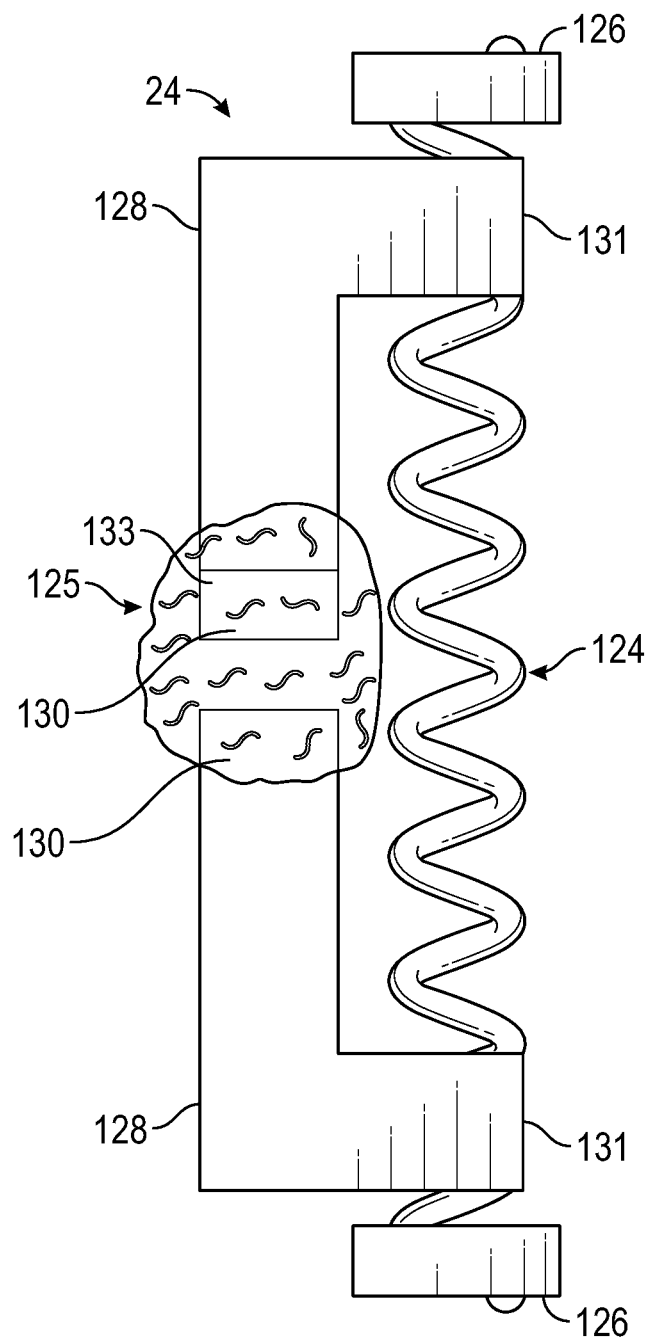
FIG. 18 is a side view of a collapsible strut or strut clip embodiment combined with a spring.
Figure 19:
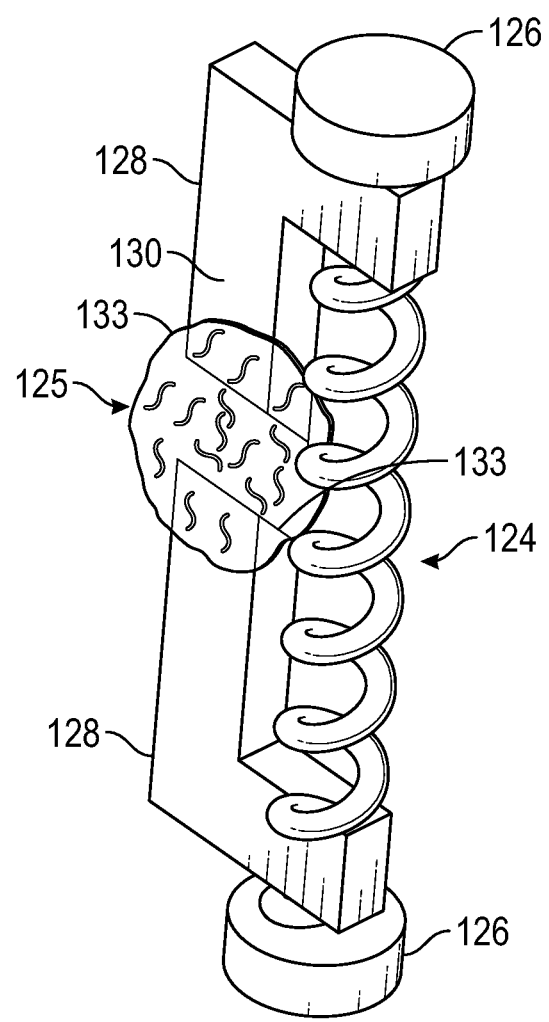
FIG. 19 is a perspective view of a collapsible strut or strut clip embodiment combined with a spring.

In still other embodiments (See FIGS. 18-19) the Strut 24 may be a bracket comprising an upper and lower L-shaped strut clip 128. The strut clips may or may not be hydrophilic. The strut clips 128 may be joined together at their proximal ends 130. Their respective distal ends 131 are coupled to the ends of the extendedly stressed spring 124 or to the mounting plates 126, if used. The proximal ends 130 may be joined mechanically offset, or they may be beveled 133, so that when the hydrophilic material deteriorates, the bracket collapses without binding, thereby allowing the spring 124 to retract to its relaxed position and close the capsule. In other embodiments the upper and lower L-shaped strut clips 128 may be joined mechanically with a hydrophobic material where the joint is then disrupted by electro-mechanical means, or by sound frequency signals In some embodiments the gastrointestinal sampling device 1 can include delayed release compounds to "fix" or preserve the sample flowing in through the ports. For example, the fluid flowing into the inner capsule triggers the strut collapse. At the same time, the fluid also starts dissolving the sample preservative. When the capsule is recovered it can be kept inside the closed capsule for storage. There are several chemical approaches to preserving samples as may be known in the art but they should not have reactive effect on the microbiota. Such, a preservative may be obtained from DNA Genoteck, a subsidiary of Orasure Technologies located in Ottowa, Canada.

FIGS. 3 and 4 are cross sectional views of FIGS. 1 and 2. As can be seen in FIG. 3, strut 24 is inserted in one of the chambers 20 of receiver 25, and elastomeric filament 23 is secured to the closed end of inner casing 2.

Figure 7:
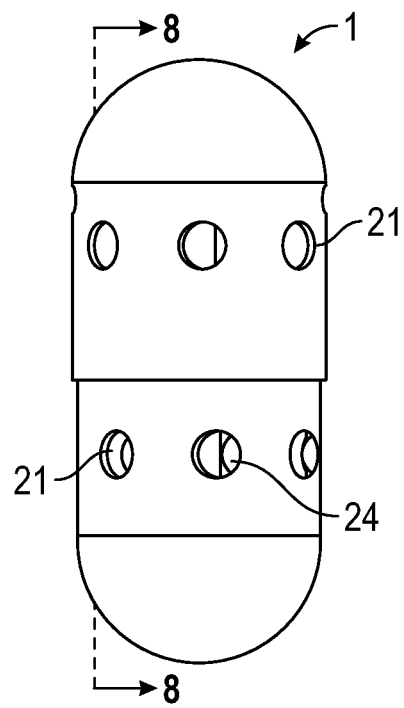
FIG. 7 is a side view of the gastrointestinal sampling device in the strutted open configuration.

FIG. 7 is a side view of the inner casing 2 partially and slideably inserted into the outer casing 4 and thereby assembled into the gastrointestinal sampling device 1 in its open configuration. As can be seen the ports 21 are all open and the strut 24 is in place keeping the device in its open configuration.

Figure 8:
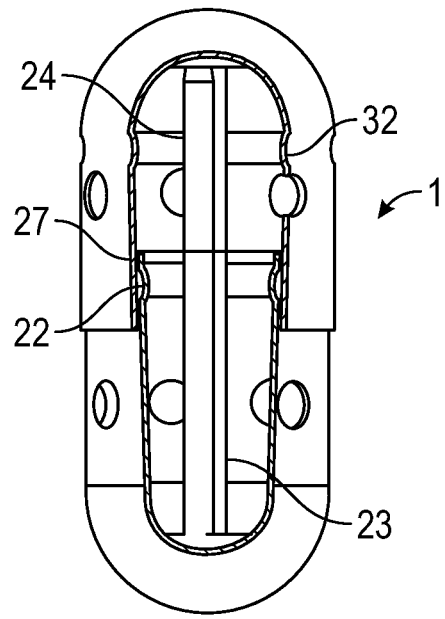
FIG. 8 is a cross sectional view of the gastrointestinal sampling device of FIG. 7.

FIG. 8 presents a cut away view of FIG. 7 revealing both the strut 24 supporting the open port configuration and elastomer band 23 providing a persistent contracting force in contravention. FIG. 8 also shows the female stop ring 22 and the male stop ring 32. When the strut 24 fails and the elastomeric filament 23 pulls the inner and outer casings (2, 4) together, the male stop ring 32 inserts itself into the female stop ring 22, thereby encouraging the gastrointestinal sampling device 1 to stay in its closed configuration along with any residual tension from the elastomeric filament 23. It should be understood that in other equivalent embodiments the stop rings 22 and 32 may be designed differently as may be known in the art with a similar effect. For example, there may be a stop ring, or rib, or edge created on the exterior side of the wall 27 that engages and stops the sliding advance of the edge of outer casing 4. Hence, the example of stop rings (22, 32) described herein is a non-limiting example.

Figure 9:
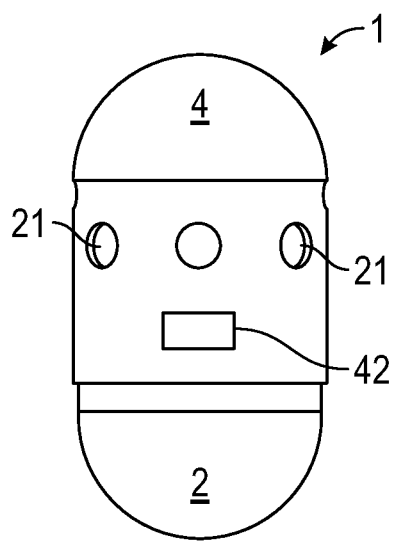
FIG. 9 is a side view of the gastrointestinal sampling device of FIG. 7 in the sealed closed configuration after the hydrophilic elastomeric filament fails.

FIG. 9 is a side view of the gastrointestinal sampling device 1 in its closed configuration. As a means of identifying one gastrointestinal sampling device 1 from another, each device may carry a radio frequency identification device (RFID) transponder 42. A RFID transponder in its various configurations and uses, per se, is well known in the art and needs not be discussed further herein.

Figure 10:
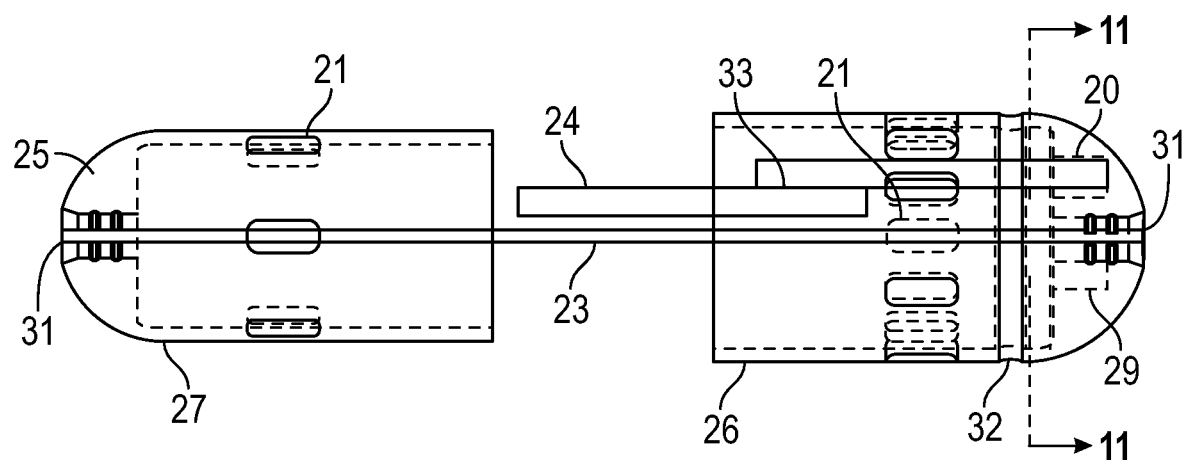
FIG. 10 depicts an exploded perspective view of a gastrointestinal sampling device according to an embodiment with a compound strut.
Figure 11:
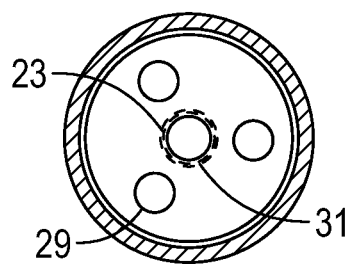
FIG. 11 is a cross sectional view of the outer ported casing of FIG. 10.

FIG. 10 is an exploded side view of another embodiment of the gastrointestinal sampling device 1. The gastrointestinal sampling device 1 is similar to that of combined FIGS. 1-2. However, the gastrointestinal sampling device 1 of FIG. 10 has one receiver 29, which is in outer casing 4 and comprises only three channels 20. The receiver 25 in inner casing 2 has no channels. In this embodiment, the strut 24 merely abuts the flat surface of the receiver 25. The strut 24 of the embodiment of FIG. 10 is a compound strut comprising two or more hydrophobic components 24A and 24B secured together by a hydrophilic attachment means 33. A non-limiting example of a hydrophilic attachment means is a polyvinyl alcohol pin, apolyvinyl alcohol band, or polyvinyl alcohol glue.

Figure 20:
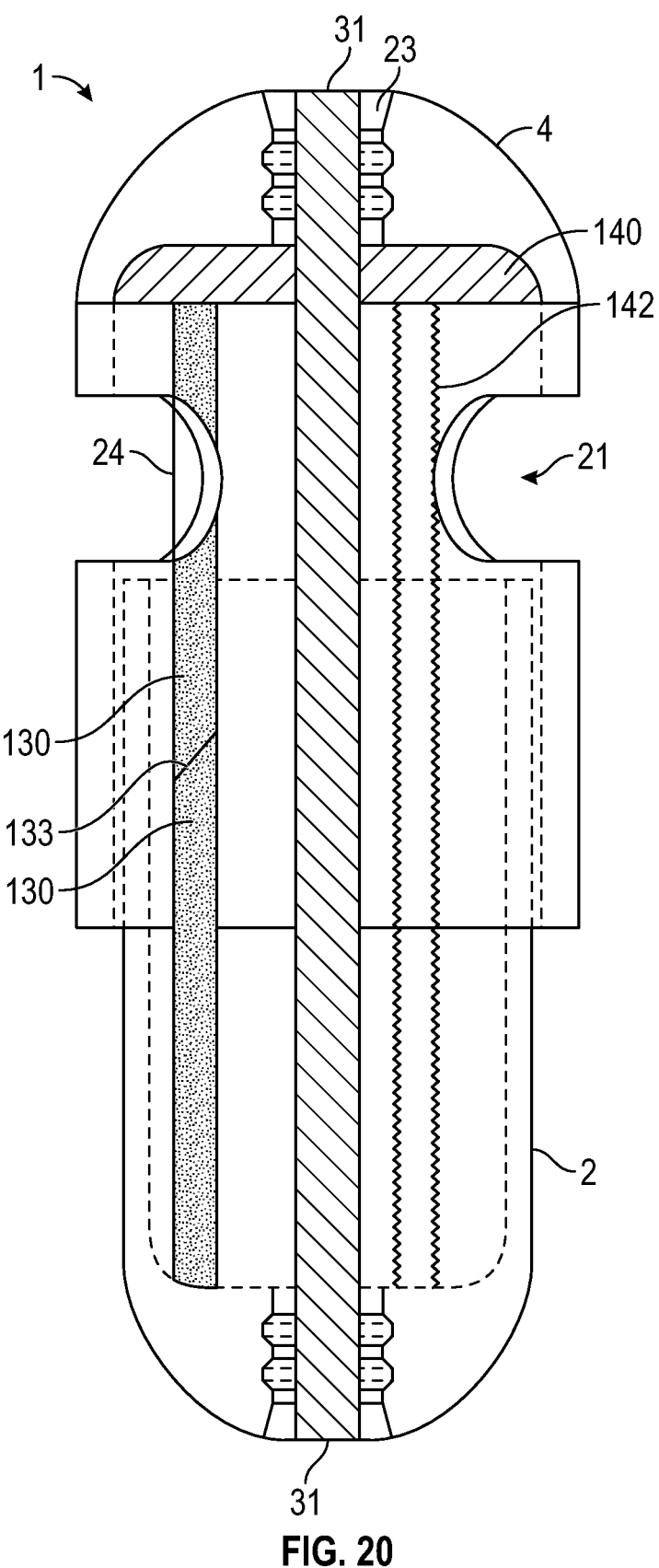
FIG. 20 is an alternative embodiment of an ingestible capsule including a free form or unsecured absorbent material, a gasket, and a free form or unsecured embodiment of a destructible strut.

In other equivalent embodiments the gastrointestinal sampling device 1 may include a pliable or an elastomeric gasket 140 penetrated with a hole. For example, FIG. 20 illustrates a non-limiting example of such a gasket. The exact size and shape if gasket 140 may vary according to the shape of the gastrointestinal sampling device 1 and as may be expedient in manufacturing, including filling the entire end portion of the outer capsule 4 and may extend into the cylindrical portion of the outer capsule 4. The purpose of the gasket is to provide a fluid tight or at least a fluid resistant seal around the edge of the inner capsule 2 to prevent fluid leakage or communication after the strut 24 has collapsed and the gastrointestinal sampling device 1 has closed.

In still other equivalent embodiments, the gastrointestinal sampling device 1 may include a sponge, absorbent material, or super absorbent material 142. The absorbent material may be a dried or pre-compressed compressed strip or stick of material that is either secured or unsecured to the inside gastrointestinal device 1. In other embodiments the dry absorbent material may circumferentially line the interior circumference of the inner capsule 2, keeping in mind that too much absorbent material may prevent the gastrointestinal sampling device 1 from closing as it expands with fluid and fills the interior of the device. A non-limiting example of absorbent material may be a non-dissolving polyvinyl alcohol foam such as that produced by Ramerfoam Technology from Honiton, Devon, Great Britain.

Figure 14:
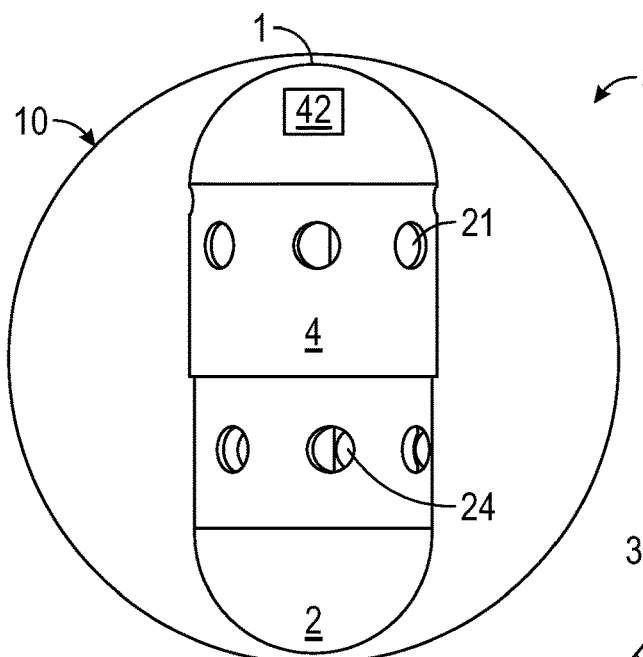
FIG. 14 is a cross sectional view of an assembled gastrointestinal sampling system in its open configuration inside a digestible outer casing.

In use as a sampling system 3 (see, FIGS. 14-15), the gastrointestinal sampling device 1 is fluidly isolated within one of a wide choice of available delayed or immediate release digestible (e.g., "enteric") outer capsule(s) 10 (see, FIG. 14) as are known in the art, and is ingested. The outer capsule 10, or parts thereof, may be chosen or designed to dissolve in an proscribed amount of time after ingestion, which implies failure of its fluid tight integrity at an approximate location along gut length x. Design parameters of the outer capsule related to time of failure of its fluid tight integrity include choice of material, thickness of the material, shape of the capsule, and mechanical weakening to intentionally create weak points in the capsule that may fail faster than a general failure. Because stomach acid ranges from a pH of 1-3.5, the outer capsule 10 may necessarily need to be acid resistant below a 3.5 pH from a few minutes for liquid stomach contents to five hours for stomach contents with meat and high fat substances. Thickness and material can adjust for this timing.

The digestible outer capsule 10 is an excipient that dissolves in the stomach or intestines in a desired timeframe thereby providing fluid access to and through the normally open ports 21 of the gastrointestinal sampling device 1. The fluid flow comprises local community microbiota along with their environment including ingesta, loosely adherent mucus layer particles, and bodily chemistries into the gastrointestinal sampling device 1. The fluid flow enters the gastrointestinal sampling device 1, envelopes the dissolvable, non-toxic strut 24 causing it to fail structurally, which in turn allows the tension provided by the elastomeric filament 23 to pull or slide the inner casing 2 further into the outer casing 4 and hold gastrointestinal sampling device 1 in a closed, sealed port position (see, FIG. 13). The capsule continues through the gastrointestinal tract and is recovered from the stool, cleaned, identified by the RFID tag 42, and can be opened for analysis or frozen for future analysis. The RFID tag contains information such as when the gastrointestinal sampling device was ingested, in what order, and the construction parameters of its digestible outer capsule 10, as non-limiting informational examples. The circuitry of the RFID tag may include a sub-circuit wherein the sub-circuit is closed when the inner capsule 1 is in the closed configuration and is open in the open configuration. As such, it can be electronically determined where the capsule is located and if it is open or closed. A device with multiple receivers or multiple transceivers may provide a location in three dimensions.

As discussed above the physical and chemical parameters of the digestible outer capsule 10 will indicate approximately where in the gastrointestinal tract the sample was taken based on an expected elapsed time to dissolution. Alternatively, the outer capsule 10 may be comprised of a material that only deteriorates in the presence of certain pH, enzymes, bacteria, or the immediate byproducts thereof.

The outer digestible capsule(s) 10 may be a standard state of the art, publicly available or proprietary, biomedical immediate or delayed release gastrointestinal capsule. One or more enteric capsules are capable of protecting the inner capsule from the strong acidity of the stomach for later disintegration in the intestines. Other non-limiting examples of possible digestible materials include polyvinyl alcohol, seaweed derivatives from the Evoware Company of Indonesia, casein proteins developed by the US Department of Agriculture, Agar, and the Cassava root from the Avani Company of Bali. Other non-limiting examples of biodigestible polymers may include Polyactic acid and Polly-3-hydroxybutyrate (PHB). Suitable proprietary materials may also be obtained from Capsugel of Morristown, Jew Jersey, USA and the Eudragit® brand of pH sensitive materials from Evonik Industries AG of Essen, Germany.

In short, any suitable medical grade dissolvable/digestible material may be used to produce the outer capsule(s) that currently exists or that may be developed in the future. The outer capsule may be approximately 25.5 mm in length with a diameter of approximately 8.7-9.95 mm.

Figure 16:
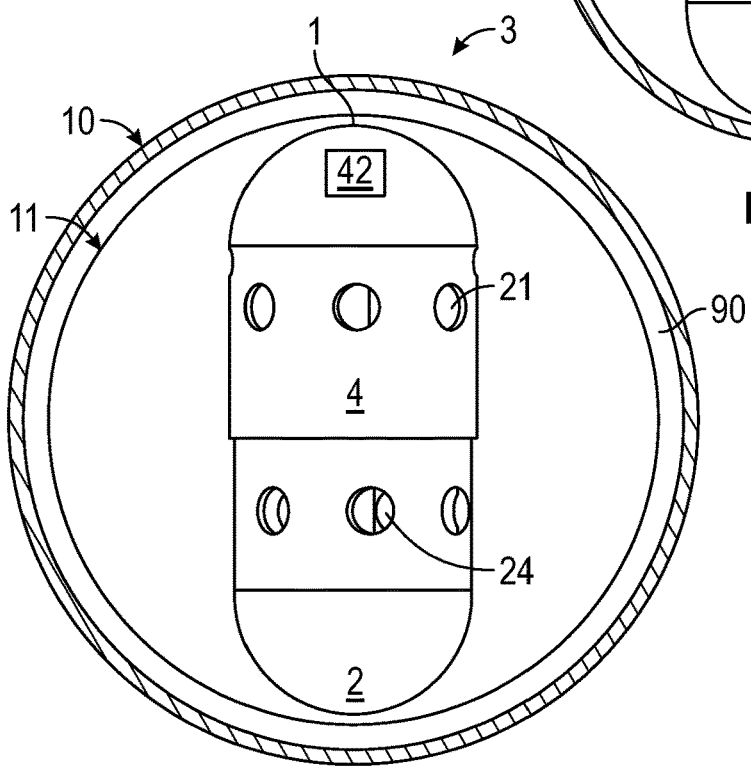
FIG. 16 is a cross sectional view of an assembled gastrointestinal provision system in its closed configuration inside a digestible outer casing and an inner thin casing.

In other embodiments, an interstitial capsule or "skin" 11 (see, FIG. 16) may be incorporated between the outer capsule 10 and the gastrointestinal sampling device 1, thereby providing a two parameter selection mechanism for taking a sample. For example, the outer capsule 10 may fail at a pH of 5.8 or less and the inner thin capsule 11 may be designed to deteriorate on contact with a certain bacteria. Only when both capsules fail will a sample be captured as discussed above.

In some embodiments, the outer capsule 10 and the interstitial capsule 11 are double ended, two part hard capsules (or half-capsules) of similar size and shape to the gastrointestinal sampling device 1, but without any ports 21. The interstitial capsule 11 may be manufactured to encapsulate and protect the gastrointestinal sampling device 1. The outer capsule 10 may be manufactured to encapsulate the interstitial capsule 11 and a delivery payload placed between at least a portion of the interstitial capsule 11 and the outer capsule 10 such that when the outer capsule dissolves the payload is released, which could be a drug, medicine or nano-structures/machines. Hence, it is contemplated herein that composition and structure of the outer capsule 10, the inner capsule 11, and hydrophilic strut 24, of the gastrointestinal sampling device 1 may be designed to fail in a specific sequence, timing, and/or a series of locations in the digestive tract.

RFID devices or circuits engineered into one or more of the nested capsules may be designed to respond while each capsule retains its original physical fluid tight integrity but cease to operate when its capsule loses its original physical fluid tight integrity. As such, device performance and its general location along the tract can be monitored in real time.

In some additional embodiments the outer half-capsule (not shown) of the outer capsule 10 comprises a first dissolvable material and may be secured fluid tight over at least part of the inner half-capsule (not shown) of the outer capsule 10 that comprises a different second dissolvable material.

The inner half-capsule (not shown) of the outer capsule 10 may also be adhered fluid tight to part of the outside of the interstitial capsule 11. A designed space between the interstitial capsule 11 and the inner half-capsule of the outer capsule 10 may contain a payload comprising a medicine, a drug, or a number of nano-structures that are thereby protected from digestive fluids for a desired travel time to a particular location. The rounded outer half capsule (not shown) of the outer capsule 10 may be comprised of a fast dissolving substance such as gelatin that falls away in or just after exiting the stomach and be desired for ease of swallowing. The inner half-capsule of the outer capsule 10 is of such a material and thickness to provide the desired travel time for the payload.

Figure 15:
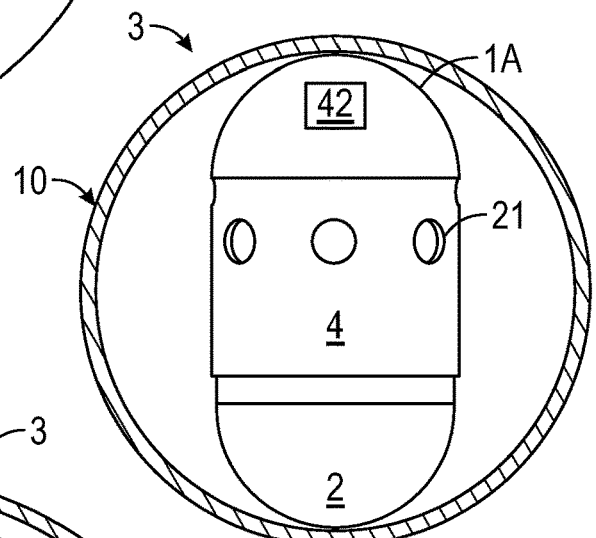
FIG. 15 is a cross sectional view of an assembled gastrointestinal provision system in its closed configuration inside a digestible outer casing.

Further, the gastrointestinal sampling system 3 may include other embodiments of ingestible capsule 10 that may be used independently or in conjunction with the ingestible capsule 1A of FIG. 15. For example, FIG. 15 depicts another embodiment of the gastrointestinal sampling device 1A, that may operate to deliver a drug, device or other substance to a targeted area of the digestive tract. In this embodiment, the strut 24 and elastomeric filament 23 of FIG. 1 both may be replaced with a compressed spring 124. Or alternatively, the strut 24 may be shortened and a compressed spring 124 added to the end being inserted into the outer casing 2. The casings (2, 4) may then be filled with a medicine or drug and then the casings compressed together and inserted into a digestible outer capsule 10 of such dimensions so as to keep the gastrointestinal delivery device 1A in its closed configuration. The outer capsule 10 may be constructed of such a material and construction that the patient's digestion causes the outer capsule 10 to fail at an expected location in the digestive track, thereby releasing the payload substance as the spring 15 forces the gastrointestinal delivery device 1A into its open configuration. Non-limiting exemplary payloads may be any of medicines, chemical substances, enzymes, antibiotics, proteins, fecal matter, fecal transplants, nanostructures, nano-robots, and microbes.

An exemplary technique using a coordinated set of gastrointestinal sampling devices 1 and 1A may include two separate sampling devices 1 and one delivery device 1A being ingested at the same time with slightly different-to dissolution time settings built into the material of the outer capsules 10. The three devices should travel relatively close together through the digestive tract. Timing differences may be constructed into each capsule such that a first sampling device 1 triggers into its closed configuration capturing a "before" sample. A specified time later the delivery device 1A triggers into its open configuration to release a medicine. And, at a third time the second sampling device 1 triggers into its closed configuration to take a second "after" sample of the material that should still be in the proximity of the first sample.

In still further embodiments, the sampling capsule system 1 disclosed herein may be used in conjunction with nano-objects, such as a nanobox with or without an articulating lid, to more efficiently deliver substances and collect samples. A non-limiting example of a nano-object is a DNA/RNA Origami object that is more fully described in U.S. Pat. No. 9,765,341 issued Sep. 9, 2017 to Bachelet and U.S. Pat. No. 9,944,923 issued Apr. 17, 2018 to Blattman, each of which is herein incorporated by reference in its entirety.

Figure 21:
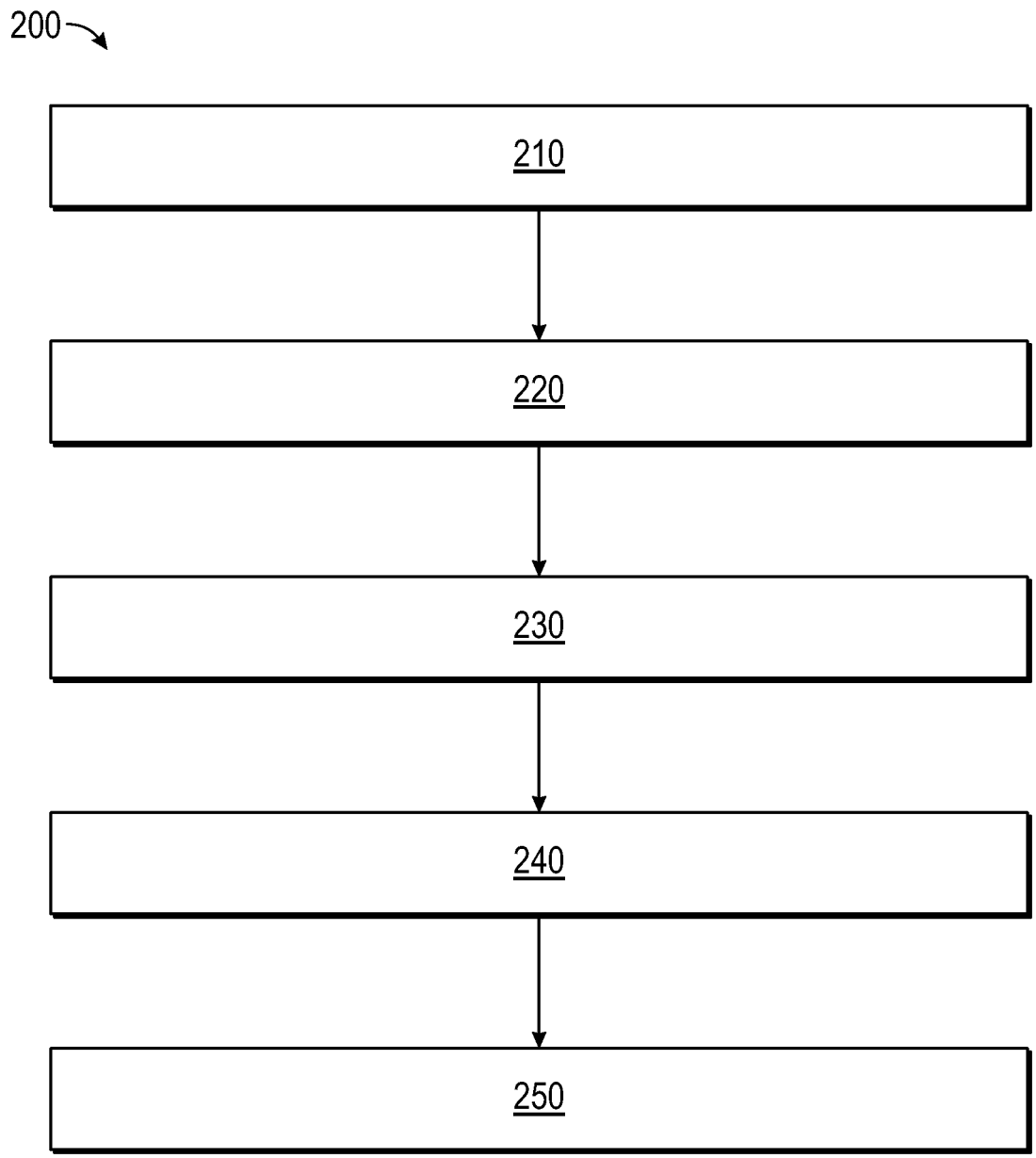
FIG. 21 is a block flow diagram of a sample capsule operating method.

FIG. 21 is an exemplary logic flow chart illustrating a method 200 of operation of the three capsule sampling system 3 based on a single exemplary embodiment of the capsule. Those skilled in the art will find modifications of the structure of the capsule useful to meet specific operational requirements. Hence, FIG. 21 is merely illustrative and is not intended to limit the scope of the inventions disclosed herein.

At process 210, the assembled capsule sampling system 3 is ingested. In some embodiments the capsule sampling system 3 may be configured to have an interstitial space 90 (See e.g., FIG. 16) between the outer capsule 10 and the interstitial capsule 11. Outer capsule 10 and interstitial capsule 11 may be comprised of a double ended, two part, oblong capsule without any ports in a similar oblong shape of a sampling capsule 1. Such an interstitial space 90 may be located in one end of the oblong shaped outer capsule 10 although such a location is not intended to be limiting. Selecting a specific half capsule having a longer specific length relative to the corresponding half capsule of an oblong interstitial capsule 11 is one way of controlling the existence and size of the interstitial space.

The two half capsules of the outer capsule 10 may be designed to dissolve in different pH liquids. In this example, the half-outer-capsule that does not contain the drug payload may have a pH tolerance of 6.5 or higher and therefor dissolves in the acidic stomach fluids (pH 1.0-3.5) almost immediately at process 220 and exposing only half of the interstitial capsule 11.

The second half-outer-capsule that contains the drug payload may have a pH sensitivity of 6 or higher and is adhered fluid tight to the outside surface of the interstitial capsule 11, thereby fluidly isolating the drug payload in the interstitial space. As such, the second half outer capsule does not dissolve in the acidic stomach fluid but is passed into the intestines (pH 6-7.4) along with the intact drug payload at process 230. The pH of the intestines are known to vary from location to another along the tract. As such, the pH sensitivity of the second half-outer-capsule may be selected so that the second half-outer-capsule dissolves at a specific pH in a targeted location and releases the drug payload at process 240. It should be noted that instead of gluing, other means of fluid tightly attaching the inside of the outer capsule to the outside of a more inner capsule may include a friction fit circumferential male/female collar arrangement that may or may not include a o-ring.

The intact interstitial capsule 11 travels through the intestines having a different pH sensitivity than the second half capsule of the outer capsule. At process 250, the interstitial capsule dissolves at the targeted location based on local pH, thereby allowing local fluids to enter the open ports 21 of the sampling capsule 1. The sampling capsule 1, then shuts when the hydrophilic strut 24 dissolves and collapses, thereby capturing and fixing a fluid sample as further described herein.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A sampling capsule, comprising:
    a ported first casing with an open end, a closed end, a length, an inner surface, and an outer surface,
    a second casing with an open end, a closed end, a length, an inner surface, and an outer surface, wherein the outer surface of the open end of one of the first casing and the second casing slideably engages the inner surface of the open end of the other casing permitting a sliding transition of the inner capsule from an open configuration to a fluid tight, closed configuration.

2. The sampling capsule of claim 1, wherein the length of one of the first casing and the second casing is greater than the other casing.

3. The sampling capsule of claim 2, wherein the casing with the shorter length includes a gasket arranged in its closed end that is configured to engage the open end of the casing with the longer length to effect the fluid tight, closed configuration.

4. The sampling capsule of claim 1, further comprising an absorbent element contained within the capsule.

5. The sampling capsule of claim 1, wherein the capsule contains a plurality of nano-structures configured to perform one or both of releasing a substance and collecting a substance.

6. The sampling capsule of claim 5, wherein the plurality of nano-structures comprises DNA/RNA origami.

7. The sampling capsule of claim 4, wherein the absorbent element is comprised of polyvinyl alcohol foam.

8. The sampling capsule of claim 1 further comprising a second, digestible outer capsule that envelops the sampling capsule and is enveloped itself by a first digestible capsule, wherein the second digestible capsule is formulated to fail based on different environmental factors than the first digestible capsule.

9. A gastrointestinal sampling device comprising:
    a hollow capsule having a first casing with a length, a closed end, and an open end and having a ported second casing with a length, a closed end, and an open end, wherein the length of one of the first casing and the second casing is longer than the length of the other casing;
    an elastomeric filament having a length fixedly securing the closed end of the first casing to the closed end of the second casing; and
    a hydrophilic strut that spaces the closed end of the inner casing away from the closed end of the outer casing when intact, wherein the open end of the first casing envelopes the open end of the second casing leaving the ports of the second casing unobstructed as long as the hydrophilic strut is structurally intact.

10. The sampling device of claim 9, further comprising an absorbent element.

11. The sampling device of claim 9, further comprising a gasket located athwart the closed end of one of the first casing and the second casing.

12. The sampling device of claim 9, wherein the hydrophilic strut has a length sufficient to place the sampling device in an open configuration wherein the ports are unobstructed and a tension is induced in the elastomeric filament.

13. A gastrointestinal sampling system comprising:
    a hollow capsule having a first casing with a closed end and an open end, the open end slidingly engaged within a second casing also having a closed end and an open end; and
    an elastomeric filament attaching the closed end of the first casing to the closed end of the second casing.

14. The gastrointestinal sampling system of claim 13 further comprising a hydrophilic strut spacing apart the closed end of the first casing from the closed end of the second casing, thereby imparting a tension in the hydrophobic elastomeric filament.

15. The gastrointestinal sampling system of claim 14 further comprising a temporarily fluid tight outer capsule enveloping the hollow capsule.

16. The gastrointestinal sampling system of claim 15, including a radio frequency ID (RFID) device uniquely identifying the sampling system.

17. The gastrointestinal sampling system of claim 16, wherein a circuit of the RFID device is configured to detect and transmit whether the hollow capsule is in an open configuration or a closed configuration.

18. A gastrointestinal sampling system comprising:
    an ingestible means for capturing a sample of gastrointestinal microbiota and content;
    a destructible means for maintaining the ingestible means for capturing a sample of gastrointestinal microbiota and content in an open configuration; and
    a means for collapsing the ingestible means for capturing a sample of gastrointestinal microbiota and content from the open configuration into a closed configuration.

19. The gastrointestinal sampling system of claim 18 further comprising a means for fixing gastrointestinal microbiota and content.

20. The gastrointestinal sampling system of claim 19, wherein the means for fixing gastrointestinal microbiota and content is a nano-structure.

21. An unpowered gastrointestinal sampling device, comprising:
- a hollow capsule further comprising:
  - a first casing with a closed end and an open end, and
  - a second casing with a first end, a second end, and at least one sampling port being configured to permit a fluid flow into a sampling chamber
  - formed by the first casing and the second casing; and,
  - an absorbent material contained in the capsule that is configured to expand to fill over half of the sampling chamber upon contact with the fluid flow.

* * * * *